United States Patent [19]

Junino et al.

[11] Patent Number: 5,672,759
[45] Date of Patent: Sep. 30, 1997

[54] DYE COMPOSITION FOR KERATINIC FIBRES CONTAINING SULFURED METAPHENYLENEDIAMINES, DYEING PROCESS AND NEW SULFURED METAPHENYLENEDIAMINES AND PREPARATION METHOD THEREOF

[75] Inventors: Alex Junino, Livry-Gargan; Alain Genet, Aulnay-sous-Bois; Alain Lagrange, Chatou, all of France

[73] Assignee: L'Oreal, France

[21] Appl. No.: 605,264

[22] Filed: Jan. 19, 1996

Related U.S. Application Data

[62] Division of Ser. No. 456,814, Jun. 1, 1995, Pat. No. 5,534,037, which is a continuation of Ser. No. 133,051, filed as PCT/FR93/00148, Feb. 12, 1993, abandoned.

[30] Foreign Application Priority Data

Feb. 14, 1992 [FR] France ................... 92 01704
Feb. 14, 1992 [FR] France ................... 92 01705

[51] Int. Cl.$^6$ ................... C07C 323/32; C07C 233/03
[52] U.S. Cl. ................... 564/440; 564/154; 564/218; 564/219; 564/305; 564/443
[58] Field of Search ................... 8/411, 406, 407, 8/408, 416; 564/305, 306, 442, 162, 154, 218, 219, 440, 443

[56] References Cited

U.S. PATENT DOCUMENTS

| | | | |
|---|---|---|---|
| 1,940,757 | 12/1933 | Lehmann et al. | 8/411 |
| 3,705,870 | 12/1972 | Darmory et al. | 260/30.2 R |
| 4,259,261 | 3/1981 | Bugaut et al. | 564/99 |
| 4,863,482 | 9/1989 | Junino et al. | 8/429 |

FOREIGN PATENT DOCUMENTS

| | | |
|---|---|---|
| 0303826 | 2/1989 | European Pat. Off. . |
| 0331144 | 9/1989 | European Pat. Off. . |
| 1061331 | 4/1954 | France . |
| 2362116 | 3/1978 | France . |
| 3343642 | 6/1985 | Germany . |
| 3724642 | 2/1989 | Germany . |

*Primary Examiner*—Shailendra Kumar
*Attorney, Agent, or Firm*—Cushman Darby & Cushman IP Group of Pillsbury Madison & Sutro

[57] ABSTRACT

The invention relates to a dye composition for keratinic fibers comprising an oxidation colorant precursor of the type ortho and/or para and a sulfured metaphenylenediamine having formula (I)

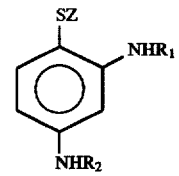

wherein Z is alkyl, aralkyl, monohydroxyalkyl or polyhydroxyalkyl, aryl or aminoalkyl, as well as the acid salts thereof, with the condition that $R_1$ and $R_2$ do not represent simultaneously hydrogen when Z is alkyl or hydroxyalkyl, as well as the acid salts corresponding to the compounds of formula (I).

2 Claims, No Drawings

DYE COMPOSITION FOR KERATINIC FIBRES CONTAINING SULFURED METAPHENYLENEDIAMINES, DYEING PROCESS AND NEW SULFURED METAPHENYLENEDIAMINES AND PREPARATION METHOD THEREOF

This is division of application Ser. No. 08/456,814 filed Jun. 1, 1995, now U.S. Pat. No. 5,534,037 which is a continuation of application Ser. No. 08/133,051, filed as PCT/FR93/00148, Feb. 12, 1993, now abandoned.

The present invention relates to new dyeing compositions for keratinous fibers containing sulfur-containing meta-phenylenediamines, to a process for dyeing in alkaline medium using these compositions, to new sulfur-containing meta-phenylenediamines as well as to a process for preparing them.

Sulfur-containing derivatives of aromatic amines have already been used, combined with oxidation dye precursors, in the presence of an oxidizing agent and alkali metal salts in acidic, neutral or basic medium for dyeing keratinous fibers. Such compositions are described in patent DE 593 061.

It is known to dye keratinous fibers and in particular human hair, with dyeing compositions containing oxidation dye precursors and couplers. DE-A-3,343,642 describes such compositions containing, as coupler, a 6-hydroxyalkylthio-1,3-diaminobenzene.

Couplers, also called color modifiers, make it possible to vary the shades obtained with oxidation dye precursors.

In the field for dyeing keratinous fibers and in particular human hair, couplers are being searched for which, combined with oxidation dye precursors, make it possible to obtain a broad range of shades, while conferring in the hair a color having a satisfactory resistance to light, to washing, to adverse weather conditions, to perspiration and to the various treatments to which the hair may be subjected.

The applicants have just discovered, and this constitutes the subject of the invention, that the use of sulfur-containing meta-phenylenediamines of formula (I) as coupler with ortho and/or pard type oxidation dye precursors makes it possible to obtain, at neutral, acidic or alkaline pH, after application to the keratinous fibers and in particular human hair, a broad range of shades of color exhibiting a particularly remarkable resistance to light, to washing, to adverse weather conditions, to perspiration and to the various treatments to which the hair may be subjected.

One subject of the invention therefore consists of oxidative dyeing compositions intended to be used for dyeing keratinous fibers and in particular human hair, containing at least one ortho and/or para type oxidation dye precursor and at least one sulfur-containing meta-phenylenediamine of formula (I) below.

Another subject of the invention is the process for dyeing keratinous fibers and in particular human hair, using such a composition mixed with an oxidizing agent.

The subject of the invention is also new sulfur-containing meta-phenylenediamines as well as a process for preparing them and their use in dyeing compositions for keratinous fibers. Other subjects of the invention will emerge on reading the following description and examples.

The subject of the present invention is therefore the dyeing compositions for keratinous fibers and in particular human hair, containing, in a medium suitable for dyeing, at least one ortho and/or para type oxidation dye precursor and at least, as coupler, one sulfur-containing meta-phenylenediamine of formula:

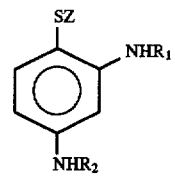

in which:

Z represents a $C_1$–$C_{18}$ alkyl radical, an aralkyl radical in which the alkyl radical corresponds to $C_1$–$C_6$, a monohydroxy($C_1$–$C_6$ alkyl) or polyhydroxy($C_2$–$C_6$ alkyl) radical, an aryl radical, an aminoalkyl radical of formula:

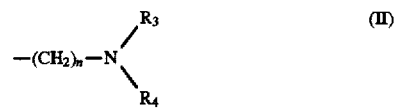

in which n is an integer between 1 and 6 inclusive, $R_3$ and $R_4$, which are identical or different, represent a hydrogen atom or $C_1$–$C_4$ alkyl, hydroxy($C_1$–$C_4$ alkyl) or $C_2$–$C_6$ acyl radical; $R_1$ and $R_2$, which are identical or different, represent a hydrogen atom, a $C_1$–$C_6$ alkyl radical, a monohydroxy ($C_1$–$C_6$ alkyl), polyhydroxy($C_2$–$C_6$ alkyl), monocarbamyl ($C_1$–$C_6$ alkyl), dicarbamyl($C_1$–$C_6$ alkyl), amino($C_1$–$C_6$ alkyl), $C_2$–$C_6$ acyl, $C_2$–$C_6$ carbalkoxy, carbamyl or mono ($C_1$–$C_6$ alkyl)carbamyl radical, with the proviso that $R_1$ and $R_2$ do not simultaneously designate a hydrogen atom when Z designates an alkyl or hydroxyalkyl radical, as well as the acid salts corresponding to the compounds of formula (I).

Among the preferred meanings of the Z radical in the sulfur-containing meta-phenylenediamines of general formula (I) according to the invention, the $C_1$–$C_{18}$ alkyl radical designates methyl, ethyl, propyl, butyl, dodecyl or hexadecyl radicals; the aralkyl radical designates the benzyl radical; the mono- or polyhydroxyalkyl radical designates —$CH_2$—$CH_2OH$, —$CH_2$—$CHOH$—$CH_2$—$OH$, —$CH_2$—$CHOH$—$CH_3$; the aryl radical designates phenyl; the aminoalkyl radical designates —$CH_2$—$CH_2$—$NH_2$;

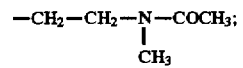

—$CH_2$—$CH_2$—$NHCH_3$; —$CH_2$—$CH_2$—$NHCOCH_3$;
when the R groups represent an acyl radical, the latter preferably designates formyl, acetyl and propionyl radicals.

The acid salts corresponding to the sulfur-containing meta-phenylenediamine compounds of general formula (I) are preferably chosen from the hydrochlorides, the sulfates or the hydrobromides.

Among the sulfur-containing meta-phenylenediamines of general formula (I), the particularly preferred compounds are:

6-methylthio-1,3-di$\beta$-hydroxyethylamino)benzene 6-methylthio-1-N-($\beta$-hydroxyethylamino-3-aminobenzene 6-($\beta$-acetylaminoethylthio)-1,3-diaminobenzene 6-methylthio-3-N-$\beta$-hydroxyethylaminoaniline 6-methylthio-3-acetylaminoaniline 6-($\beta$-acetylaminoethylthio)-3-acetylaminoaniline 6-($\beta$-acetylaminoethylthio)-3-amino-1-acetylaminobenzene and their salts.

The compounds of formula (I) can be used as coupler in the presence of ortho and/or para type oxidation dye precursors known per se, which make it possible to dye the hair by oxidative dyeing, according to a process using a reaction of oxidative condensation of the precursors with the coupler.

The ortho or para type dye precursors are compounds which are not dyes per se, but which form a dye by a process of oxidative condensation, either with themselves, or in the presence of a coupler or modifier.

These ortho or para type oxidation dye precursors are benzene or heterocyclic compounds comprising two amino or amino and hydroxy functional groups in the ortho or para position with respect to each other.

The ortho or para type oxidation dye precursors may be chosen from para-phenylenediamines, para-aminophenols, para heterocyclic precursors derived from pyridine or pyrimidine, such as 2,5-diaminopyridine, 2-hydroxy-5-aminopyridine, 2,4,5,6-tetraaminopyrimidine, 4,5-diamino-1-methylpyrazole, 2-dimethylamino-4,5,6-triaminopyrimidine, ortho-aminophenols and the so-called "double" bases.

As para-phenylenediamines, there may be mentioned more particularly the compounds corresponding to the formula (III):

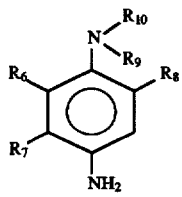

in which:

$R_6$, $R_7$, $R_8$, which are identical or different, represent a hydrogen or halogen atom, an alkyl radical, an alkoxy radical, a carboxy, sulfo or hydroxy($C_1$–$C_4$ alkyl) radical; $R_9$ and $R_{10}$, which are identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl or morpholinoalkyl radical or a phenyl radical optionally substituted in the para position by an amino group, or alternatively $R_9$ and $R_{10}$ form, together with the nitrogen atom to which they are attached, a piperidino or morpholino heterocycle, provided that $R_6$ or $R_8$ represents a hydrogen atom when $R_9$ and $R_{10}$ do not represent a hydrogen atom, as well as the salts of these compounds. These alkyl or alkoxy groups have 1 to 4 carbon atoms and especially designate the methyl, ethyl, propyl, methoxy and ethoxy radical.

Among the compounds of formula (III), there may be mentioned more particularly para-phenylenediamine, p-toluylenediamine, methoxyparaphenylenediamine, chloroparaphenylenediamine, 2,3-dimethylparaphenylenediamine, 2,6-dimethylparaphenylenediamine, 2,6-diethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, N,N-diethylparaphenylenediamine, N,N-dipropylparaphenylenediamine, 3-methyl-4-amino-N,N-diethylaniline, N,N-di-(β-hydroxyethyl)paraphenylenediamine, 3-methyl-4-amino-N,N-di(β-hydroxyethyl)aniline, 3-chloro-4-amino-N,N-di(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl, β-piperidinoethyl)aniline, 3-methyl-4-amino-N,N-(ethyl, β-piperidinoethyl)aniline, 4-amino-N,N-(ethyl, β-morpholinoethyl)aniline, 3-methyl-4-amino-N,N-(ethyl, β-morpholinoethyl)aniline, 4-amino-N,N-(ethyl, β-acetylaminoethyl)aniline, 4-amino-N-(β-methoxyethyl) aniline, 3-methyl-4-amino-N,N-(ethyl, β-acetylaminoethyl) aniline, 4-amino-N,N-(ethyl, β-mesylaminoethyl)aniline, 3-methyl-4-amino-N,N-(ethyl, β-mesylaminoethyl)aniline, 4-amino-N,N-(ethyl, β-sulfoethyl)aniline, 3-methyl-4-amino-N,N-(ethyl, β-sulfoethyl)aniline, N-[(4'-amino)phenyl]morpholine, N-[(4'-amino)phenyl]piperidine, 2-hydroxyethylparaphenylenediamine, fluoroparaphenylenediamine, carboxyparaphenylenediamine, sulfoparaphenylenediamine, 2-isopropylparaphenylenediamine, 2-n-propylparaphenylenediamine, hydroxy-2-n-propylparaphenylenediamine, 2-hydroxymethylparaphenylenediamine, N,N-dimethyl-3-methylparaphenylenediamine, N,N-(ethyl, β-hydroxyethyl)paraphenylenediamine, N-(dihydroxypropyl)paraphenylenediamine, N-4'-aminophenylparaphenylenediamine, N-phenylparaphenylenediamine.

These para-phenylenediamines can be introduced into the dyeing composition either in the form of a free base or in the form of salts, such as hydrochloride, hydrobromide or sulfate.

Among the p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 3-(β-hydroxyethoxy)-4-aminophenol, 2-methoxymethyl-4-aminophenol, 2-aminomethyl-4-aminophenol, 2-β-hydroxyethylaminomethyl-4-aminophenol, 2-ethoxymethyl-4-aminophenol, 2-(β-hydroxyethoxy) methyl-4-aminophenol.

The so-called "double" bases are bis-phenylalkylenediamines corresponding to the formula:

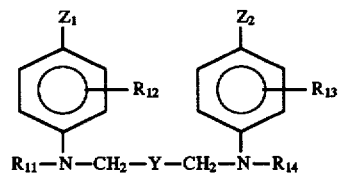

in which:

$Z_1$ and $Z_2$, which are identical or different, represent hydroxyl or $NHR_{15}$ groups, where $R_{15}$ designates a hydrogen atom or a lower alkyl radical;

$R_{12}$ and $R_{13}$, which are identical or different, represent either hydrogen atoms or halogen atoms or alternatively alkyl radicals;

$R_{11}$ and $R_{14}$, which are identical or different, represent a hydrogen atom, an alkyl, hydroxyalkyl or aminoalkyl radical whose amino residue may be substituted; Y represents a radical chosen from the group consisting of the following radicals:

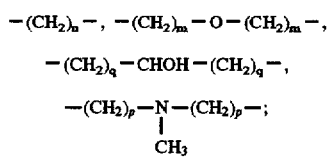

in which n is an integer between 0 and 8 and m, q and p are integers between 0 and 4, it being possible for this base to exist also in the form of its addition salts with acids.

The alkyl or alkoxy radicals indicated above preferably designate a group having 1 to 4 carbon atoms and especially methyl, ethyl, propyl, methoxy and ethoxy.

Among the compounds of formula (IV), there may be mentioned N,N'-bis(β-hydroxyethyl)-N,N'-bis(4,-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine.

Among the ortho-aminophenols, there may be mentioned more particularly 1-amino-2-hydroxybenzene, 6-methyl-1-hydroxy-2-aminobenzene, 4-methyl-1-amino-2-hydroxybenzene, 4-acetylamino-1-amino-2-hydroxybenzene.

The dyeing compositions conforming to the invention may also contain, in addition to the coupler corresponding to the formula (I) defined above, other couplers known per se, such as meta-diphenols, meta-aminophenols, meta-phenylenediamines different from those of formula (I) above, meta-acylaminophenols, meta-ureidophenols, meta-carbalkoxyaminophenols, α-naphthol, indole derivatives, couplers possessing an active methylene group such as the β-ketone compounds, pyrazolones.

Among these couplers, there may be more particularly mentioned 2,4-dihydroxyphenoxyethanol, 2,4-dihydroxyanisole, meta-aminophenol, resorcinol monomethyl ether, resorcinol, 2-methylresorcinol, 2-methyl-5-aminophenol, 2-methyl-5-N-(β-hydroxyethyl)aminophenol, 2-methyl-5-N-(β-mesylaminoethyl)aminophenol, 2,6-dimethyl-3-aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]phenoxyethanol, 2-amino-4-N-(β-hydroxyethyl)aminoanisole, (2,4-diamino)phenyl-β-γ-dihydroxypropyl ether, 2,4-diaminophenoxyethylamine, 1,3-dimethoxy-2,4-diaminobenzene, 1,3,5-trimethoxy-2,4-diaminobenzene, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, 6-methoxy-3-hydroxyethylaminoaniline, 1-ethoxy-2-bis(β-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy-1,3-diaminobenzene, 4-methyl-6-ethoxy-1,3-diaminobenzene, 4-chloro-6-methyl-3-aminophenol, 6-chloro-3-trifluoroethylaminophenol, and their salts.

There may be added to these compositions, as is well known in the prior state of the art, especially for the purpose of imparting a shade to or increasing the shimmer of the colors provided by the oxidation dye precursors, direct dyes such as azo or anthraquinone dyes or the nitro derivatives of the benzene series.

The entire para and/or ortho type oxidation dye precursors, as well as the couplers used in the dyeing compositions conforming to the invention, preferably represent 0.3 to 7% by weight relative to the weight of the said composition. The concentration of sulfur-containing meta-phenylenediamine compounds of formula (I) may vary between 0.05 and 3.5% by weight of the total weight of the composition.

The dyeing compositions conforming to the invention also contain in their preferred embodiment, anionic, cationic, non-ionic or amphoteric surface-active agents or mixtures thereof. Among these surface-active agents, there may be mentioned alkyl benzenesulfonates, alkyl naphthalenesulfonates, sulfates, ether sulfates and sulfonates of fatty alcohols, quaternary ammonium salts such as trimethylcetylammonium bromide, cetylpyridinium bromide, ethanolamides of optionally oxyethylenated fatty acids, polyglycerolated fatty alcohols, polyoxyethylenated or polyglycerolated alkylphenols, as well as polyoxyethylenated alkyl sulfates.

These surface-active agents are present in the compositions conforming to the invention in proportions of between 0.5 and 55% by weight, and preferably between 2 and 50% by weight relative to the total weight of the composition.

These compositions may also contain organic solvents for solubilizing the components which may not be sufficiently soluble in water. Among these solvents, there may be mentioned by way of example, $C_1$–$C_4$ lower alkanols such as ethanol and isopropanol; glycerol; glycols or glycol ethers such as 2-butoxyethanol, ethylene glycol, propylene glycol, monoethyl ether and monomethyl ether of diethylene glycol, as well as aromatic alcohols such as benzyl alcohol or phenoxyethanol, analogous products and mixtures thereof.

The solvents are preferably present in proportions of between 1 and 40% by weight, and in particular between 5 and 30% by weight relative to the total weight of the composition.

The thickening agents which may be added to the compositions conforming to the invention may be chosen from sodium alginate, gum arabic, optionally crosslinked acrylic acid polymers, cellulose derivatives, heterobiopolysaccharides such as xanthan gum, inorganic thickening agents such as bentonite may also be used. These thickening agents are preferably present in proportions of between 0.1 and 5%, and in particular between 0.2 and 3% by weight relative to the total weight of the composition.

The antioxidants which may be present in the compositions are chosen in particular from sodium sulfite, thioglycolic acid, sodium bisulfite, dehydroascorbic acid, hydroquinone and homogentisic acid. These antioxidants are present in the composition in proportions of between 0.05 and 1.5% by weight relative to the total weight of the composition.

These compositions may also contain other cosmetically acceptable adjuvants, such as for example penetrating agents, sequestering agents, perfumes, buffers and the like.

The compositions conforming to the invention may be provided in various forms, such as in the form of a liquid, cream or gel or in any other form appropriate for dyeing keratinous fibers and especially human hair. These compositions may be packaged in aerosol bottles in the presence of a propelling agent and may form foams.

The dyeing compositions conforming to the invention containing a para and/or ortho type oxidation dye precursor and a coupler of formula (I), are used according to a process involving developing by means of an oxidizing agent.

In conformity with this process, the dyeing composition described above is mixed, at the time of use, with an oxidizing solution in a sufficient quantity so as to be able to develop a color, then the mixture obtained is applied to the keratinous fibers and in particular human hair.

The pH of the composition applied to the hair varies between 3 and 11. It is adjusted to the desired value by means of alkalinizing agents well known in the prior state of the art, such as ammonium hydroxide, alkali metal carbonates, alkanolamines such as mono-, di- and triethanolamine, as well as their derivatives or sodium or potassium hydroxides, or by means of conventional acidifying agents such as inorganic or organic acids such as hydrochloric, tartaric, citric, phosphoric and sulfonic acids. The oxidizing solution contains, by way of oxidizing agent, hydrogen peroxide, urea peroxide, persalts such as ammonium persulfate or alkali metal bromates. A solution of hydrogen peroxide at 20 volumes is preferably used.

The mixture obtained is applied to the hair and it is allowed to act for 10 to 40 minutes, preferably 15 to 30 minutes, after which the hair is rinsed, washed with shampoo, rinsed again and dried.

The coupler of formula (I) defined above may also be used in a multistage process, consisting in one of the stages, in applying the ortho and/or para type oxidation dye precursor or a mixture thereof and, in another stage, in applying a dyeing composition containing the coupler of formula (I).

The oxidizing agent may be introduced, just before the application, into the composition applied in the second phase or alternatively applied to the keratinous fibers themselves, in a third phase, the exposure, pH, washing and drying conditions being identical to those indicated above.

Another object of the invention consists of the new sulfur-containing meta-phenylenediamines of formula (I) above, as well as their salts with an acid.

The subject of the invention is also the use of these sulfur-containing meta-phenylenediamines in dyeing compositions for keratinous fibers.

The sulfur-containing meta-phenylenediamines of formula (I) or their salts can be prepared according to multistage processes.

According to a first process and in a first stage, bromo-2,4-dinitrobenzene is reacted, in the presence of a base such as potassium hydroxide or potassium carbonate, with a thiol of formula (V):

$$z'-SH \qquad (V)$$

in which Z' represents a $C_1-C_{18}$ alkyl radical, an aralkyl radical in which the alkyl radical corresponds to $C_1-C_6$, a monohydroxy($C_1-C_6$ alkyl) radical, a polyhydroxy($C_2-C_6$ alkyl) radical or a group of formula (VI)

in which $R_3$ and n have the meanings indicated above in formula (I); and $R_5$ represents a hydrogen atom or a $C_1-C_3$ alkyl radical;

in a second stage, the nitro substituents of the compound of formula (VII):

obtained above are reduced in order to prepare a compound corresponding to formula (VIII):

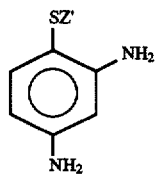

in which Z' has the meaning indicated above;

optionally, in a third stage, and depending on the sulfur-containing meta-phenylenediamine compound of formula (I) which it is desired to obtain, there is performed a) either a mono-substitution of the aromatic amines in order to obtain a compound of formula (I) in which $R_1$ and/or $R_2$ are different from H b) or an acid hydrolysis of the compound (VIII) in which Z' represents

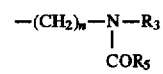

in order to obtain the compound of formula (IX)

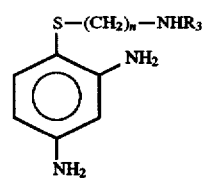

in which $R_3$ and n have the meanings indicated above, $R_3$ however not designating a $C_2-C_6$ acyl radical, it being possible for the nuclear amines then to be monosubstituted, c) or a substitution of the extranuclear amine is performed beforehand on the compound of formula (VIII) in order to obtain the compound of formula (X)

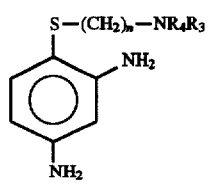

in which $R_3$, $R_4$ and n have the meanings indicated above, it being possible for the nuclear amines then to be monosubstituted.

The reduction of the nitro groups of the compounds of formula (VII) is preferably carried out using iron in acetic medium or alternatively by means of cyclohexene in the presence of a palladium-carbon catalyst or by any other conventional reduction process.

The substitution of the aromatic amines or of the extranuclear amine can be carried out by reacting for example ethyl bromide, glycol bromohydrin, ethyl chloroformate, β-chloroacetamide, or acetic anhydride.

According to a second process and in a first stage, a substituted fluoronitrobenzene of formulae (XIa) or (XIb)

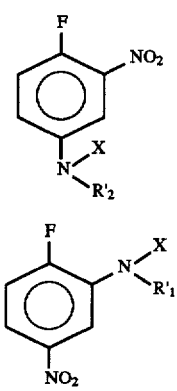

(XIa)

(XIb)

in which R'₁ and R'₂ represent a $C_2$–$C_6$ acyl group and X represents a hydrogen atom, or alternatively R'₂ and X or R'₁ and X form, together with the nitrogen atom to which they are attached an oxazolidone ring, is reacted with a thiol of formula:

$$Z'—SM \qquad (XII)$$

in which M is an alkali metal and Z' has the meanings indicated above;

in a second stage, the nitro substituent of the compound of formulae (XIIIa) or (XIIIb)

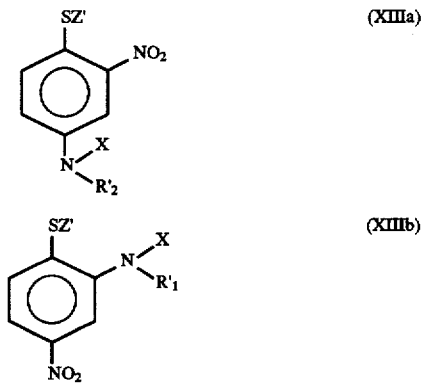

(XIIIa)

(XIIIb)

obtained above is reduced in order to prepare a compound corresponding to the formula (XIVa) or (XIVb):

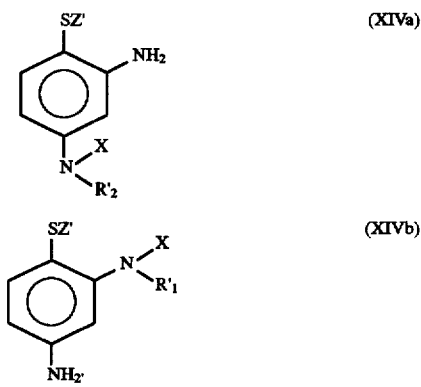

(XIVa)

(XIVb)

in which R'₁, R'₂ and X have the meanings indicated above; optionally, in a third stage, and depending on the sulfur-containing meta-phenylenediamine compound of formula (I) which it is desired to obtain, a monosubstitution of the aromatic amines is performed in order to obtain a compound of formula (I) in which R₂ and/or R'₂ are different from H Lastly, in a final stage, the compound is subjected to an acid hydrolysis so as to cut the protecting group X.

The following examples are intended to illustrate the invention without, however, being restrictive in nature.

EXAMPLE 1

Preparation of 6-methylthio-1,3-di(β-hydroxyethylamino) benzene dihydrochloride

1st stage:
Synthesis of 6-methylthio-1,3-di(β-chlorocarbethoxyamino) benzene 14.5 ml of β-chloroethyl chloroformate are added dropwise to a suspension of 15.9 g (0.07 mole) of 6-methylthio-1,3-diaminobenzene and 28 g of calcium carbonate in 12 ml of dioxane, heated in a boiling water bath.

After heating for 30 min, this suspension is poured into 500 ml of ice cold water acidified with 60 ml of a concentrated hydrochloric acid solution.

An oil crystallizes.

It is drained, reimpasted in water and dried at 45° C. over phosphoric anhydride and under vacuum.

White crystals (24.4 g) are obtained which, after recrystallization from isopropanol, melt at 119° C. and whose elemental analysis calculated for $C_{13}H_{16}N_2O_4SCl_2$ is:

| Analysis | C | H | N | O | S | Cl |
|---|---|---|---|---|---|---|
| Theory % | 42.52 | 4.39 | 7.63 | 17.43 | 8.73 | 19.31 |
| Found % | 42.72 | 4.48 | 7.61 | 17.54 | 8.61 | 19.24 |

2nd stage:
Alkaline hydrolysis

The compound obtained in the 1st stage (22.8 g–0.062 mole) is suspended in 54 ml of 96% ethanol, 27 ml of water and 54 ml of 10N caustic soda.

The suspension is heated at the reflux temperature of the alcohol until complete hydrolysis (10 min) of the oxazolidone intermediate is obtained.

The reaction is monitored by thin-layer chromatography (silica gel; eluant: ethyl acetate).

The alcohol is evaporated under reduced pressure, a brown oil is obtained in suspension to which 100 ml of ice cold water are added and the mixture is extracted with ethyl ether (about 500 ml).

The ethereal phase is dried over sodium sulfate and filtered. 20 ml of an approximately 7N hydrochloric acid solution in absolute ethanol are added thereto.

The dihydrochloride precipitates as oil which crystallizes.

After draining, washing with ethyl ether and drying over potassium hydroxide, white crystals (18.4 g) are obtained which melt with decomposition at 158°–160° C. and whose elemental analysis calculated for $C_{11}H_{20}N_2O_2SCl_2$ is:

| Analysis | C | H | N | O | S | Cl |
|---|---|---|---|---|---|---|
| Theory % | 41.91 | 6.39 | 8.89 | 10.15 | 10.17 | 22.49 |
| Found % | 41.89 | 6.42 | 8.90 | 10.27 | 10.08 | 22.58 |

EXAMPLE 2

Preparation of 6-methylthio-1-N-β-hydroxyethylamino-3-aminobenzene.

1st stage.
Synthesis of 6-methylthio-3-acetylaminonitrobenzene

At room temperature, 50.0 g of sodium thiomethoxide are suspended in 500 ml of dimethoxyethane and 99.1 g (0.5 mole) of 2-nitro-4-acetylaminofluorobenzene are added, in portions, over 30 min, while the temperature is maintained between 25° and 27° C. by means of an ice cold water bath.

After leaving to stir for an additional 30 min at 25°–27° C., this suspension is poured into 4 liters of ice cold water.

The orange-yellow crystallized precipitate is drained, reimpasted in water and dried over phosphoric anhydride.

107.0 g of orange crystals are obtained which melt at 178° C. after recrystallization from 96% ethanol, and whose elemental analysis calculated for $C_9H_{10}N_2O_3S$ is:

| Analysis | C | H | N | O | S |
| --- | --- | --- | --- | --- | --- |
| Theory % | 47.78 | 4.45 | 12.38 | 21.21 | 14.17 |
| Found % | 47.90 | 4.40 | 12.48 | 21.01 | 14.10 |

2nd stage:
Synthesis of 6-methylthio-3-acetylamino-1-aminobenzene.

A suspension of 0.5 g of ammonium chloride and 17 g of zinc in the form of a fine powder in 40 ml of 96% ethanol and 3.6 ml of water is heated at the reflux temperature of the alcohol.

6.8 g (0.03 mole) of the compound obtained during the 1st stage are added in portions so as to maintain the reflux without heating (an exothermic decolorization is observed).

After the end of the addition, the reflux is maintained for 20 min.

The mixture is filtered in the boiling state and the zinc slurry is washed with minimum hot alcohol.

The filtrate is diluted with two volumes of ice cold water. The expected compound crystallizes slowly.

After draining, washing with water, drying over phosphoric anhydride and recrystallization from isopropanol, 2.6 g of white crystals are obtained which melt at 105° C. and whose elemental analysis calculated for $C_9H_{12}N_2OS$ is:

| Analysis | C | H | N | O | S |
| --- | --- | --- | --- | --- | --- |
| Theory % | 55.08 | 6.16 | 14.27 | 8.15 | 16.34 |
| Found % | 55.07 | 6.18 | 14.11 | 8.32 | 16.31 |

3rd stage
Synthesis of 6-methylthio-1-β-chlorocarbethoxyamino-3-acetylaminobenzene.

This compound is prepared according to the procedure described in Example 1 (1st stage).

White crystals are obtained which, after recrystallization from ethyl acetate, have a melting point of 162° C., and whose elemental analysis calculated for $C_{12}H_{15}N_2O_3SCl$ is:

| Analysis | C | H | N | O | S | Cl |
| --- | --- | --- | --- | --- | --- | --- |
| Theory % | 47.60 | 4.99 | 9.25 | 15.85 | 10.59 | 11.71 |
| Found % | 47.76 | 5.07 | 9.05 | 16.05 | 10.43 | 11.60 |

4th stage
Alkaline hydrolysis

The alkaline hydrolysis of the compound obtained in the preceding stage is carried out according to the procedure described in Example 1 (2nd stage).

After recrystallization from acetonitrile, a white crystalline compound is obtained with a yield of 69%, whose melting point is 96° C. and whose elemental analysis calculated for $C_9H_{14}N_2OS$ is:

| Analysis | C | H | N | O | S |
| --- | --- | --- | --- | --- | --- |
| Theory % | 54.52 | 7.12 | 14.13 | 8.07 | 16.17 |
| Found % | 54.60 | 7.16 | 14.11 | 8.20 | 15.98 |

EXAMPLE 3

Preparation of 6-methylthio-3-N-β-hydroxyethylaminoaniline dihydrochloride.
1st stage
Synthesis of 3-(4-methylsulfanyl-3-nitrophenyl)oxazolidin-2-one.

The procedure described in Example 1 (1st stage) is used.

Starting with 45.2 g (0.2 mole) of 3-(4-fluoro-3-nitrophenyl)oxazolidin-2-one, 48.5 g of orange crystals are obtained which, after recrystallization from dimethoxyethane, have a melting point of 180° C. and whose elemental analysis calculated for $C_{10}H_{10}N_2O_4S$ is:

| Analysis | C | H | N | O | S |
| --- | --- | --- | --- | --- | --- |
| Theory % | 47.24 | 3.96 | 11.02 | 25.17 | 12.61 |
| Found % | 47.20 | 3.99 | 11.06 | 25.43 | 12.49 |

2nd stage:
Synthesis of 6-methylthio-3-N-β-hydroxyethylaminonitrobenzene.

The alkaline hydrolysis of the preceding compound is carried out according to the procedure described in Example 1 (2nd stage).

Dark red crystals are obtained with a yield of whose melting point is 104° C. and whose elemental analysis calculated for $C_9H_{12}N_2O_3S$ is:

| Analysis | C | H | N | O | S |
| --- | --- | --- | --- | --- | --- |
| Theory % | 47.36 | 5.30 | 12.27 | 21.03 | 14.05 |
| Found % | 47.34 | 5.38 | 12.34 | 21.20 | 13.89 |

3rd stage
The reduction of the preceding compound is carried out according to the procedure used for Example 2 (2nd stage).

The dihydrochloride crystallizes from the reaction medium filtered after addition of hydrochloric absolute ethanol.

White crystals are obtained which melt with decomposition at 154°–157° C. and whose elemental analysis calculated for $C_9H_{16}N_2OSCl_2$ is:

| Analysis | C | H | N | O | S | Cl |
| --- | --- | --- | --- | --- | --- | --- |
| Theory % | 39.86 | 5.95 | 10.30 | 5.90 | 11.82 | 26.14 |
| Found % | 39.92 | 6.05 | 10.32 | 6.10 | 11.66 | 25.98 |

EXAMPLE 4

Preparation of 6-(β-acetylaminoethylthio)-1,3-diaminobenzene dihydrochloride.
1st stage
Synthesis of 6-(β-acetylaminoethylthio)-3-nitro-1-acetylaminobenzene.

20 g of powdered potassium hydroxide are dissolved in a solution of 71.4 g (0.6 mole) of β-acetylaminoethylthiol in 300 ml of dimethoxyethane heated to 45° C.

After cooling to 30° C., 47.5 g (0.24 mole) of 2-acetylamino-4-nitrofluorobenzene are added in portions, over 30 min.

The suspension is kept at 30°–35° C. for 30 min.

The reaction medium is poured into 800 ml of ice cold water. The yellow crystalline precipitate is drained, reimpasted in water and dried over phosphoric anhydride.

Yellow crystals (67.3 g) are obtained which, after recrystallization from ethanol, melt at 172° C. and whose elemental analysis calculated for $C_{12}H_{15}N_3O_4S$ is

| Analysis | C | H | N | O | S |
|---|---|---|---|---|---|
| Theory % | 48.48 | 5.09 | 14.13 | 21.52 | 10.78 |
| Found % | 48.69 | 5.16 | 14.00 | 21.74 | 10.80 |

2nd stage
Synthesis of 6-(β-acetylaminoethylthio)-3-amino-1-acetylaminobenzene.

The reduction is carried out according to the procedure described for Example 2 (2nd stage). A white crystalline compound is obtained whose melting point is 148° C. and whose elemental analysis calculated for $C_{12}H_{17}N_3O_2S$ is:

| Analysis | C | H | N | O | S |
|---|---|---|---|---|---|
| Theory % | 53.91 | 6.41 | 15.72 | 11.97 | 11.99 |
| Found % | 53.95 | 6.39 | 15.90 | 12.08 | 11.95 |

3rd stage

The deacetylation of the amino group in position 1 is carried out by heating, at 80° C. for 5 hours, a solution of 20 g (0.74 mole) of the compound obtained in the preceding stage in 300 ml of a normal hydrochloric acid solution.

The mixture is cooled and neutralized with a 20% ammonium hydroxide solution.

After extraction with ethyl acetate, drying over sodium sulfate, filtration and evaporation to dryness, the oil obtained and purified by passing over a medium-pressure column (silica gel—eluant: mixture of ethyl and heptane). The dihydrochloride is prepared in hydrochloric absolute ethanol and precipitated by diluting with ethyl ether. The mixture is drained and dried over potassium hydroxide.

The white crystals (4.7 g) melt with decomposition at 201°–204° C. The mass spectrum is in conformity with the expected product.

EXAMPLES OF DYEING PROCESSES

Examples 1 to 4

Composition A

| | |
|---|---|
| Octyl dodecanol sold under the name EUTANOL D by the company HENKEL | 8.0 g |
| Oleic acid | 20.0 g |
| Monoethanolamine lauryl ether sulfate sold under the name SIPON LM 35 by the company HENKEL | 3.0 g |
| Ethyl alcohol | 10.0 g |
| Benzyl alcohol | 10.0 g |
| Cetylstearyl alcohol containing 33 moles of ethylene oxide sold under the name SIMULSOL GS by the company SEPPIC | 2.4 g |
| Ethylenediaminetetraacetic acid | 0.2 g |
| Aqueous solution containing 60% of | 3.7 g AI |
| AI of a cationic polymer having the following recurring unit: 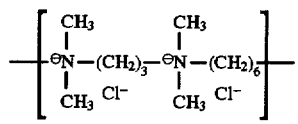 | |
| Monoethanolamine | 7.5 g |
| Linoleic acid diethanolamide sold under the name COMPERLAN F by the company HENKEL | 8.0 g |
| Ammonium hydroxide containing 20% $NH_3$ | 10.2 g |
| Sodium metabisulfite in aqueous solution at 35% | 1.3 g |
| Hydroquinone | 0.15 g |
| Dyes | x g |
| Demineralized water qs | 100.0 g |

Composition B

Hydrogen peroxide at 20 volumes and at pH=3.

Dyeing procedure

The composition A is mixed, weight for weight, with the composition B. The mixture obtained is applied to natural gray hair which is 90% white, permanently waved or otherwise, for 30 min. The hair is then rinsed, washed with shampoo and then rinsed again and dried.

| EXAMPLES | 1 | 2 | 3 | 4 |
|---|---|---|---|---|
| (in g) Composition A containing: | | | | |
| 6-methylthio-3-N-β-hydroxy-ethylaminoaniline, dihydrochloride | 0.54 | | | |
| 6-methylthio-1-N-β-hydroxy-ethylamino-3-aminobenzene | | 0.40 | | |
| 6-methylthio-1,3-di(β-hydroxy-ethylamino)benzene, dihydrochloride | | | 0.63 | |
| 6-(β-acetylaminoethylthio)-1,3-di-aminobenzene, dihydrochloride | | | | 0.60 |
| Para-phenylenediamine | 0.22 | 0.22 | 0.22 | 0.22 |
| Mixture of A and B weight for weight | | | | |
| pH of the mixture | 10.2 | 10.3 | 10.5 | 10.3 |
| Shades obtained | | | | |
| On natural gray hair which is 90% white | | bluish-gray | pearly gray | |
| On permanently waved natural gray hair which is 90% white | intense pearly ashen | | | ash blond |

Examples 5 to 9

Composition A

| | |
|---|---|
| Polyglycerolated oleyl alcohol containing 2 moles of glycerol | 4.0 g |
| Polyglycerolated oleyl alcohol containing 4 moles of glycerol containing 78% of AI | 5.69 g AI |
| Oleic acid | 3.0 g |
| Oleylamine containing 2 moles of ethylene oxide sold under the name ETHOMEEN O12 by the company AKZO | 7.0 g |
| Diethylaminopropyl lauryl amino-succinamate, sodium salt, containing 55% of AI | 3.0 g AI |
| Oleyl alcohol | 5.0 g |

| | |
|---|---|
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite in aqueous solution at 35% | 0.455 g |
| Ammonium acetate | 0.8 g |
| Antioxidant, sequestrant qs | |
| Perfume, preservatives qs | |
| Monoethanolamine qs pH 9.8 | |
| Dyes | x g |
| Demineralized water qs | 100.0 g |

Composition B

It consists of a solution of hydrogen peroxide at 20 volumes whose pH is adjusted to between 1 and 1.5 with orthophosphoric acid.

Dyeing procedure

The composition A is mixed, weight for weight, with the composition B of hydrogen peroxide. The mixture obtained is applied to natural gray hair which is 90% white, permanently waved or otherwise, for 30 minutes. The hair is then rinsed, washed with shampoo, then rinsed again and dried.

| EXAMPLES | 5 | 6 | 7 | 8 | 9 |
|---|---|---|---|---|---|
| (in g) Composition A containing: | | | | | |
| 6-methylthio-3-N-β-hydroxy-ethylaminoaniline, dihydrochloride | 0.81 | | | | |
| 6-methylthio-1,3-diaminobenzene, dihydrochloride | | 0.68 | | | |
| 6-methylthio-1-N-β-hydroxy-ethylamino-3-aminobenzene | | | 0.59 | | |
| 6-methylthio-1,3-di(β-hydroxy-ethylamino)benzene, dihydrochloride | | | | 0.95 | |
| 6-(β-acetylaminoethylthio)-1,3-di-aminobenzene, dihydrochloride | | | | | 1.19 |
| 2,6-dimethylpara-phenylenediamine | 0.41 | 0.41 | 0.41 | 0.41 | 0.54 |
| Mixture of A and B weight for weight | | | | | |
| pH of the mixture | 6.2 | 6.2 | 6.5 | 6.2 | 6.0 |
| Shades obtained | | | | | |
| On natural gray hair which is 90% white | | intense blue | | ash blue | peacock blue |
| On permanently waved natural gray hair which is 90% white | intense ash blue | | ash blue | | |

We claim:

1. A sulfur-containing meta-phenylenediamine having the formula

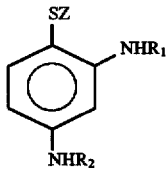

(I)

wherein

Z represents $C_1$–$C_{18}$ alkyl, aralkyl wherein the alkyl moiety has 1–6 carbon atoms, $C_1$–$C_6$ monohydroxyalkyl, $C_2$–$C_6$ polyhydroxyalkyl, aryl, aminoalkyl having the formula

(II)

wherein n is an integer ranging from 1 to 6 and $R_3$ and $R_4$, each independently, represent hydrogen, $C_1$–$C_4$ alkyl, $C_1$–$C_4$ hydroxyalkyl or $C_2$–$C_6$ acyl;

$R_1$ and $R_2$, each independently, represent hydrogen, $C_1$–$C_6$ alkyl, $C_1$–$C_6$ monohydroxyalkyl, $C_2$–$C_6$ polyhydroxyalkyl, $C_1$–$C_6$ monocarbamylalkyl, $C_2$–$C_6$ dicarbamylalkyl, $C_1$–$C_6$ aminoalkyl, $C_2$–$C_6$ acyl, $C_2$–$C_6$ carbalkoxy, carbamyl or mono($C_1$–$C_6$) alkylcarbamyl, with the proviso that $R_1$ and $R_2$ do not simultaneously represent hydrogen when Z represent alkyl or hydroxyalkyl; or an acid addition salt of said sulfur-containing metaphenylenediamine of formula (I).

2. The sulfur-containing meta-phenylenediamine of claim 1 selected from the group consisting of:

6-methylthio-1,3-di(β-hydroxyethylamino)benzene, 6-methylthio-1-N-β-hydroxyethylamino-3-aminobenzene, 6-(β-acetylaminoethylthio)-1,3-diaminobenzene, 6-methylthio-3-N-β-hydroxyethylaminoaniline, 6-(β-acetylaminoethylthio)-3-amino-1-acetylaminobenzene, 6-methylthio-3-acetylaminoaniline, 6-(β-acetylaminoethylthio)-3-acetylaminoaniline and an acid addition salt thereof.

\* \* \* \* \*